United States Patent [19]

Burton et al.

[11] 4,455,314
[45] Jun. 19, 1984

[54] PENICILLIN DERIVATIVES

[75] Inventors: George Burton, Carshalton; Desmond J. Best, Southwater, both of England

[73] Assignee: Beecham Group p.l.c., England

[21] Appl. No.: 459,668

[22] Filed: Jan. 20, 1983

[30] Foreign Application Priority Data

Jan. 22, 1982 [GB] United Kingdom ............... 8201751

[51] Int. Cl.³ ................... A61K 31/43; C07D 499/56
[52] U.S. Cl. .................. 424/271; 260/239.1; 260/245.2 R
[58] Field of Search ............ 260/239.1, 245.2 R; 424/271

[56] References Cited

U.S. PATENT DOCUMENTS

| 4,260,625 | 4/1981 | Hardy et al. | 424/271 |
| 4,304,717 | 12/1981 | Huhn et al. | 260/239.1 |
| 4,385,060 | 5/1983 | Clayton et al. | 424/271 |

Primary Examiner—Natalie Trousof
Assistant Examiner—Vera C. Clarke
Attorney, Agent, or Firm—Jacobs & Jacobs

[57] ABSTRACT

The preparation and use of 6,α-methoxy-6,β-[2-(2-methylphenoxycarbonyl)-2-(thien-3-yl) acetamido] penicillanic acid of formula (II):

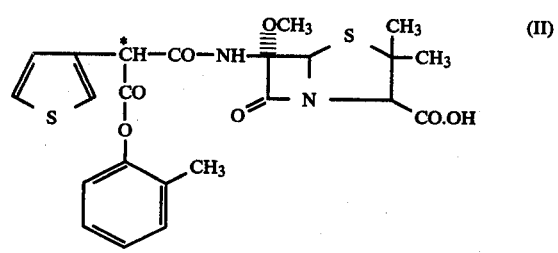

or a pharmaceutically acceptable salt or in vivo hydrolysable ester thereof.

19 Claims, No Drawings

PENICILLIN DERIVATIVES

This invention relates to penicillin derivatives and more particularly to the o-tolyl ester of an α-carboxy 6-methoxy-penicillin.

The penicillin derivative and its salts are active against Gram-negative bacteria which makes them useful as therapeutic and prophylactic agents against bacterial infections in animals, including man and domestic animals, such as cattle and poultry.

U.K. Pat. No. 1,538,051 claims a penicillin derivative of the formula (I):

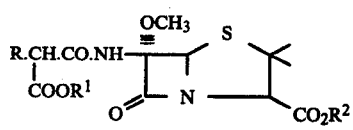

wherein R is phenyl or 2- or 3-thienyl and $R^2$ is hydrogen, a pharmaceutically acceptable salting ion or a radical which forms an ester which is hydrolysable in-vivo in man and $R^1$ is a pharmaceutically acceptable ester-forming radical.

Such esters have the advantage that they are orally absorbed in animal species, including man, where they undergo in-vivo hydrolysis to produce a degree of blood level antibiotic activity due to the free α-carboxy 6-methoxy-penicillin that is not attained when the α-carboxy 6-methoxy-penicillin itself is orally administered to the animal species.

The present invention is based on the discovery that the α-ortho-tolyl ester of α-carboxy-3-thienylmethyl 6-methoxy-penicillin exhibits higher bioavailability after oral administration in mammals, such as man than other esters such as, for example, the phenyl ester.

Accordingly, this invention provides 6β-[2-(2'-methylphenoxycarbonyl)-2-thien-3'-ylacetamido]-6α-methoxy penicillanic acid of formula (II):

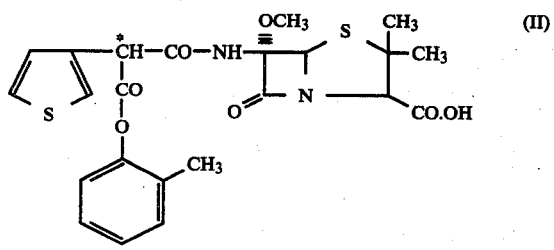

or a pharmaceutically acceptable salt or in vivo hydrolysable ester thereof.

The compounds of the present invention include the pharmaceutically acceptable esters of the 3-carboxylic acid group which hydrolyse readily in the human body to produce the parent acid, for example acyloxyalkyl groups such as acetoxymethyl, pivaloyloxymethyl, α-acetoxyethyl, α-acetoxybenzyl and α-pivaloyloxyethyl groups; alkoxycarbonyloxyalkyl groups, such as ethoxycarbonyloxymethyl and α-ethoxycarbonyloxyethyl; dialkylaminoalkyl groups such as dimethylaminomethyl, dimethylaminoethyl, diethylaminomethyl or diethylaminoethyl; and lactone groups such as phthalidyl or dimethoxyphthalidyl.

Suitable salts of the 3-carboxylic acid group of the compound of formula (II) include metal salts, eg aluminium, alkali metal salts such as sodium or potassium, alkaline earth metal salts such as calcium or magnesium, and ammonium or substituted ammonium salts, for example those with lower alkylamino such as triethylamine, hydroxy-lower alkylamines such as 2-hydroxyethylamine, bis-(2-hydroxyethyl)-amine or tri-(2-hydroxyethyl)-amine, cycloalkylamines such as bicyclohexylamine, or with procaine, dibenzylamine, N,N-dibenzylethylenediamine, 1-ephenamine, N-ethylpiperidine, N-benzyl-β-phenethylamine, dehydroabeitylamine, N,N'-bisdehydroabietylethylenediamine, or bases of the pyridine type such as pyridine, collidine or quinoline, or other amines which have been used to form salts with known penicillins.

The carbon atom marked * in formula (II) is asymmetric. This invention includes both optically active isomers at that position as well as the D,L-mixture.

The compounds of formula (II) may be prepared by reacting a compound of formula (III):

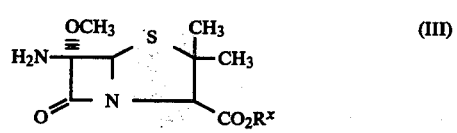

wherein the amino group is optionally substituted with a removable group which permits acylation to take place and wherein $R^x$ is a carboxyl blocking group; with an N-acylating derivative of an acid of formula (IV):

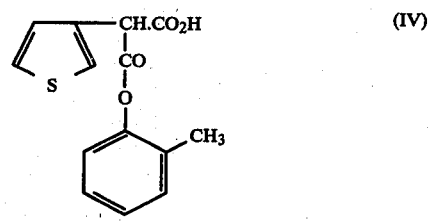

and thereafter if necessary carrying out one or more of the following steps:

(i) removal of any substituent on the amide group;
(ii) removal of any carboxyl blocking group $R^x$;
(iii) converting the product to a salt or in vivo hydrolysable ester thereof.

Suitable groups which permit acylation to take place and which are optionally present on the amino group of the starting material of the formula (III) include N-silyl, N-stannyl and N-phosphorus groups, for example trialkylsilyl groups such as trimethylsilyl, trialkyltin groups such as tri-n-butyltin, groups of formula —P.$R^aR^b$ wherein $R^a$ is an alkyl, haloalkyl, aryl, aralkyl, alkoxy, haloalkoxy, aryloxy, aralkyloxy or dialkylamino group, $R^b$ is the same as $R^a$ or is halogen or $R^a$ and $R^b$ together form a ring; suitable such phosphorus groups being —P(OC$_2$H$_5$)$_2$, —P(C$_2$H$_5$)$_2$,

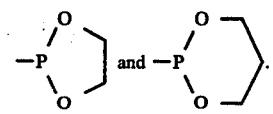

Suitable carboxyl-blocking derivatives for the group —CO$_2$R$^x$ in formula (III) include salts, ester, and anhydride derivatives of the carboxylic acid. The derivative is preferably one which may readily be cleaved at a later stage of the reaction. Suitable salts include inorganic salts, for example alkali metal salts such as the sodium salt, tertiary amine salts, such as those with tri-lower-alkylamines, N-ethylpiperidine, 2,6-lutidine, pyridine, N-methylpyrrolidine, dimethylpiperazine. A preferred salt is with triethylamine.

Suitable ester-forming carboxyl-blocking groups are those which may be removed under conventional conditions. Such groups for $R^x$ include benzyl, p-methoxybenzyl, 2,4,6-trimethylbenzyl, 3,5-di-t-butyl-4-hydroxybenzyl, benzoylmethyl, p-nitrobenzyl, 4-pyridylmethyl, 2,2,2-trichloroethyl, 2,2,2-tribromoethyl, t-amyl, diphenylmethyl, triphenylmethyl, adamatyl, 2-benzyloxyphenyl, 4-methylthiophenyl, tetrahydrofur-2-yl, tetrahydropyran-2-yl, pentachlorophenyl, p-toluenesulphonylethyl, methoxymethyl, a silyl, stannyl or phosphorus-containing group, such as described above, an oxime radical of formula $-N=CHR^o$ where $R^o$ is aryl or heterocyclic, or an in vivo hydrolysable ester radical such as defined above.

The carboxyl group may be regenerated from any of the above esters by usual methods appropriate to the particular $R^x$ group, for example, acid—catalysed hydrolysis, or by enzymatically—catalysed hydrolysis, or by hydrogenation. The hydrolysis must of course be carried out under conditions to which the ortho-tolyl ester group in the side-chain is stable.

A reactive N-acylating derivative of the acid (IV) is employed in the above process. Suitable N-acylating derivatives include an acid halide, preferably the acid chloride or bromide. Acylation with an acid halide may be affected in the presence of an acid binding agent for example tertiary amine (such as triethylamine or dimethylaniline), an inorganic base (such as calcium carbonate or sodium bicarbonate) or an oxirane, which binds hydrogen halide liberated in the acylation reaction. The oxirane is preferably a $(C_{1-6})$-1,2-alkylene oxide—such as ethylene oxide or propylene oxide. The acylation reaction using an acid halide may be carried out at a temperature in the range $-50°$ C. to $+50°$ C., preferably $-20°$ C. to $+20°$ C., in aqueous or non-aqueous media such as aqueous acetone, ethyl acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate.

The acid halide may be prepared by reacting the acid (IV) or a salt thereof with a halogenating (eg chlorinating or brominating) agent such as phosphorus pentachloride, thionyl chloride or oxalyl chloride.

Alternatively, the N-acylating derivative of the acid (IV) may be symmetrical or mixed anhydride. Suitable mixed anhydrides are alkoxyformic anhydrides, or anhydrides with, for example carbonic acid monoesters, trimethyl acetic acid, thioacetic acid, diphenylacetic acid, benzoic acid, phosphorus acids (such as phosphoric or phosphorous acids), sulphuric acid or aliphatic or aromatic sulphonic acids (such as p-toluenesulphonic acid). The mixed or symmetrical anhydrides may be generated using N-ethoxycarbonyl-2-ethoxy-1,2-dihydroquinoline. When a symmetrical anhydride is employed, the reaction may be carried out in the presence of 2,4-lutidine as catalyst.

Alternative N-acylating derivatives of acid (IV) are the acid azide, or activated esters such as esters with 2-mercaptopyridine, cyanomethanol, p-nitrophenol, 2,4-dinitrophenol, thioalcohols such as thiophenol, methanethiol, ethanethiol and propanethiol, halophenols, including pentachlorophenol, monomethoxyphenol or 8-hydroxyquionline, N-hydroxysuccinimide or 1-hydroxybenztriazole; or amides such as N-acylsaccharins or N-acylphthalimides; or an alkylidine iminoester prepared by reaction of the acid (IV) with an oxime.

Other reactive N-acylating derivatives of the acid (IV) include the reactive intermediate formed by reaction in situ with a condensing agent such as a carbodiimide, for example N,N'-diethyl-,N,N'-dipropyl- or N,N'-diisopropylcarbodiimide, N,N'-di-cyclohexylcarbodiimide; or N-ethyl-N'-γ-dimethylaminopropylcarbodiimide; a suitable carbonyl compound, for example N,N'-carbonyldiimidazole or N,N'-carbonylditriazole; an isoxasolinium salt, for example N-ethyl-5-phenylisoxazolinium-3-sulphonate or N-t-butyl-5-methylisoxazolinium perchlorate; or an N-alkoxycarbonyl-2-alkoxy-1,2-dihydroquinoline, such as N-ethoxycarbonyl-2-ethoxy-1,2-dihydroquinoline. Other condensing agents include Lewis acids (for example $BBr_3—C_6H_6$); or a phosphoric acid condensing agent such as diethylphosphorylcyanide. The condensation reaction is preferably carried out in an organic reaction medium, for example methylene chloride, dimethylformamide, acetonitrile, alcohol, benzene, dioxan or tetrahydrofuran.

Compounds of formula (II) may also be prepared by reacting a compound of formula (V):

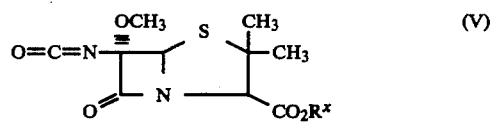

wherein $R^x$ is as defined above with respect to formula (III) above; with an acid of formula (IV) or a carbanion of formula (IVA):

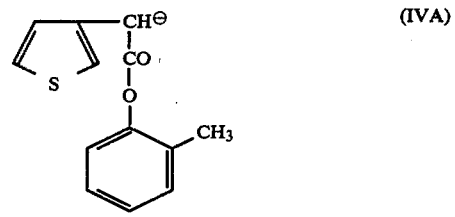

and thereafter if necessary carrying out one or more of the following steps:
  (i) removal of any carboxyl blocking group $R^x$;
  (ii) converting the product to a salt or in vivo hydrolysable ester thereof.

This reaction is preferably carried out at a temperature in the range $-10°$ to $+50°$ C. in an inert organic solvent, such as methylene dichloride, in the presence of a basic catalyst such as triethylamine, pyridine or a nitrogen-containing aromatic mono- or bi-cyclic compound such as 4-methoxy-(dimethylamino)pyridine, 1-methyl(benz)imidazole or imidazo[1,2-α]pyridine.

A third method of preparation of the compounds of formula (II) comprises:
  (a) treating a compound of formula (VI):

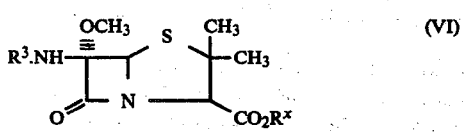

wherein R$^x$ is a carboxyl-blocking group, and R$^3$ is an acyl group, in particular an acyl group derived from the side-chain of a natural penicillin, such as benzyl penicillin or phenoxymethyl penicillin; with an agent forming an imino halide;

(b) treating the imino halide with a compound to introduce a group QR$_f$ on the imino carbon atom, wherein Q is oxygen, sulphur or nitrogen and R$_f$ is an alkyl group of from 5 to 14 carbon atoms, to form an iminoether, iminothioether, or amidine (when Q is O, S, or N respectively);

(c) reacting with an N-acylating derivative of an acid of formula (IV) above;

(d) treating with water; and (e) optionally removing the carboxyl-blocking group R$^x$.

A suitable agent for preparing an imino halide is an acid halide in the presence of an acid binding agent such as a tertiary amine, eg pyridine, triethylamine, or N,N-dimethylaniline. Examples of suitable acid halides are phosphorus pentachloride, phosgene, phosphorous pentabromide, phosphorus oxychloride, oxalyl chloride and p-toluene sulphonic acid chloride. Phosphorus pentachloride and phosphorus oxychloride are preferred. The reaction may be conducted under cooling, preferably at temperatures from 0° C. to −30° C. when phosphorus pentachloride is employed. The amount of the tertiary amine is preferably 3-5 mols per mol of phosphorus pentachloride. It is also preferable to use the phosphorus halide in an amount slightly in excess of that of the starting material.

The resulting imino compounds are then treated to introduce a —QR$_f$ group onto the imino carbon atom. This is preferably effected by reacting the imino halide with a corresponding alcohol. Examples of suitable alcohols for reaction with the imino halide are aliphatic alcohols containing from 1 to 12 carbon atoms, preferably 1 to 5 carbon atoms, such as methanol, ethanol, propanol, isopropyl alcohol, amyl alcohol and butyl alcohol, and aralkyl alcohols such as benzyl alcohol and 2-phenylethanol.

The reaction of the alcohol with the imino halide is preferably effected in the presence of an acid binding agent, such as a tertiary amine, preferably pyridine, and the reaction is usually carried out without isolating the imino halide from the reaction mixture.

Thereafter the imino compound is caused to react with an N-acylating derivative of an acid of formula (IV). The comments made above concerning such N-acylating derivatives, and the conditions for carrying out acylations also apply in this case. In particular, the presence of a tertiary amine such as pyridine or N,N-dimethylaniline in the reaction system is preferred.

Finally, the product is treated with water. The water treatment may be conducted together with the isolation of the desired material. That is the reaction mixture may be added to water or a saturated aqueous solution of sodium chloride and then the aqueous layer formed is separated from the organic solvent layer.

The compounds of formula (II) may also be prepared by esterification of a compound of formula (VII) or a salt thereof:

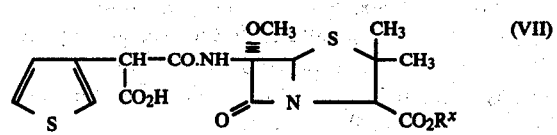

wherein R$^x$ is a carboxyl blocking group; with compound of formula (VIII):

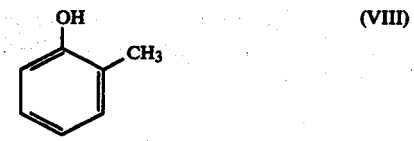

and thereafter if necessary carrying out one or more of the following steps:

(i) removal of any carboxyl blocking groups R$^x$;
(ii) converting the product to a salt or in vivo hydrolysable ester thereof.

Esterification may be performed by any conventional method, for example by reaction of the free acid with a compound of formula (VIII) in the presence of a catalyst.

Alternatively, a reactive esterifying derivative of the compound of formula (VII) may be reacted with the compound of formula (VIII) or an alkali metal or alkaline earth metal salt thereof. Suitable salts include the lithium, sodium or magnesium salts.

Reactive esterifying derivatives of the acid (VII) include the reactive intermediate formed by reaction in situ with a condensing agent such as a carbodiimide, for example N,N-diethyl-, dipropyl- or diisopropylcarbodiimide, N,N'-di-cyclohexylcarbodiimide, or N-ethyl-N'-γ-dimethylaminopropylcarbodiimide; a suitable carbonyl compound, for example N,N'-carbonyldiimidazole or N,N'-carbonylditriazole; an isoxasolinium salt, for example N-ethyl-5-phenylisoxazolinium-3-sulphonate or N-t-butyl-5-methylisoxazolinium perchlorate; or an N-alkoxycarbonyl-2-alkoxy-1,2-dihydroquinoline, such as N-ethoxycarbonyl-2-ethoxy-1,2-dihydroquinoline. Other condensing agents include Lewis acids (for example BBr$_3$—C$_6$H$_6$); or a phosphoric acid condensing agent such as diethylphosphorylcyanide. The condensation reaction is preferably carried out in an organic reaction medium, for example methylene chloride, dimethylformamide, acetonitrile, alcohol, benzene, dioxan or tetrahydrofuran.

A further method for the preparation of compounds of formula (II) comprises reacting a compound of formula (IX):

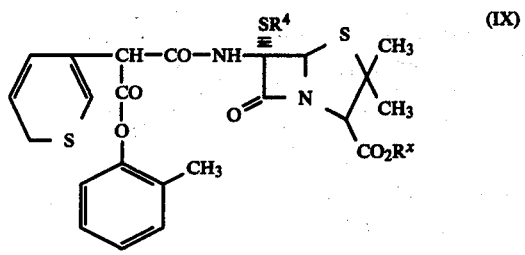

wherein $R^x$ is a carboxyl blocking group and $R^4$ is $C_{1-6}$ alkyl, benzyl or an aryl group; A) with chlorine or bromine at $-25°$ to $-80°$ C. and subsequently decomposing the resultant halosulphonium halide with methanol and a base; or B) with methanol in the presence of a metal ion, such as a tellurium (III), lead (IV), silver, copper (II), bismuth (V), mercury, lead, cadmium or thallium salt, and thereafter if necessary:

(i) removing any carboxyl blocking group;

(ii) converting the product to a salt or ester thereof. Preferably this latter reaction is carried out at $-50°$ to $+25°$ C. in a solvent.

A further method for the preparation of compounds of formula (II) comprise hydrolysis of a compound of formula (X):

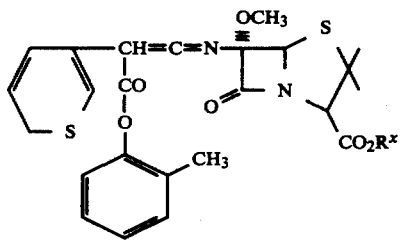

wherein $R^x$ represents a carboxyl blocking group and thereafter if necessary carrying out one or more of the following steps:

(i) removal of a carboxyl blocking group $R^x$;

(ii) converting the product to a salt or in vivo hydrolysable ester thereof.

Preferably the hydrolysis is carried out at a pH in the range 1 to 5 preferably 2 to 4, at ambient temperature. Suitable solvents include tetrahydrofuran or acetone.

The intermediate of formula (X) may be prepared by (a) treating a compound of formula (XI):

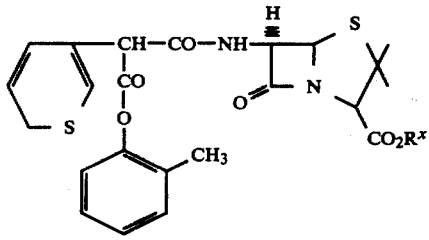

wherein $R^x$ is a carboxyl blocking group with an acid halide;

(b) treating the thus formed compound of formula (XII):

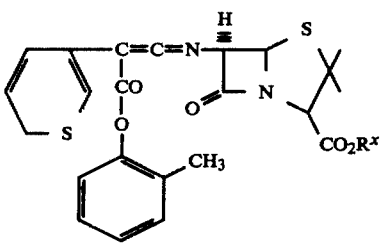

with a double bond addition reagent;

(c) reacting the resulting product with a compound of formula $CH_3OM$ wherein M is an alkali metal or thallium.

Examples of suitable acid halides are phosphorus pentachloride, phosgene, phosphorous pentabromide, phosphorus oxychloride, oxalyl chloride and p-toluene sulphonic acid chloride. Phosphorus pentachloride and phosphorus oxychloride are preferred. The reaction may be conducted under cooling, preferably at temperatures from $+5°$ C. to $-30°$ C. (preferably about $0°$ C.) when phosphorus pentachloride is employed. The amount of the tertiary amine is preferably 3-5 mols per mol of phosphorus pentachloride. It is also preferable to use the phosphorus halide in an amount in excess of that of the starting material.

Suitable double bond addition reagents for step (b) of the above process include diatomic halogen molecules or a compound of formula $Br.N_3$. Preferably the double bond addition reagent is chlorine.

The reaction is suitably carried out in an inert solvent, such as tetrahydrofuran or a halogenated hydrocarbon e.g. chloroform, at low temperatures such as $+20°$ C. to $-100°$ C. preferably $-50°$ C. to $-80°$ C., e.g. at about $-70°$ C.

The resulting product is then reacted with an alkali metal or thallium methoxide of formula $CH_3OM$. Suitably M may be sodium or potassium, but is preferably lithium. The reaction is generally carried out in a polar aprotic solvent, preferably methanol, preferably in the presence of another inert solvent, such as tetrahydrofuran as long as it does not freeze at the temperature of the reaction. The reaction is suitably carried out at low temperature, preferably in the range $-40°$ C. to $-80°$ C., preferably about $-75°$ C. The reagent $CH_3OM$ may be formed in situ by the use of methanol together with a base such as butyl lithium, lithium diisopropylamide, lithium or sodium hydride or preferably butyl lithium.

The antibiotic compounds according to the invention may be formulated for administration in any convenient way for use in human or verterinary medicine, by analogy with other antibiotics, and the invention therefore includes within its scope a pharmaceutical composition comprising a compound of formula (II) above together with a pharmaceutical carrier or excipient.

The compositions may be formulated for administration by any route, although an oral administration is preferred. The compositions may be in the form of tablets, capsules, powders, granules, lozenges, or liquid preparations, such as oral or sterile parenteral solutions or suspensions.

Tablets and capsules for oral administration may be in unit dose presentation form, and may contain conventional excipients such as binding agents for example syrup, acacia, gelatin, sorbitol, tragacanth, or polyvinyl-pyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired convention flavouring or colouring agents.

Suppositories will contain conventional suppository bases, eg cocao-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10% to 60% by weight, of the active material, depending on the method of administration. Where the compositions comprise dosage units, each unit will preferably contain from 50 to 500 mg, of the active ingredient. The dosage as employed for adult human treatment will preferably range from 100 to 3000 mg, per day, for instance 1500 mg, per day, depending on the route and frequency of administration.

The compound of formula (II) may be the sole therapeutic agent in the compositions of the invention or a combination with other antibiotics may be employed. Advantageously the compositions also comprise a compound of formula (XIII) or a pharmaceutically acceptable salt or ester thereof:

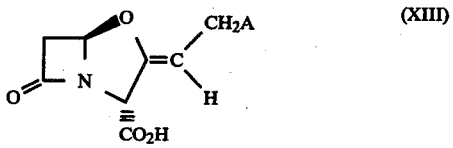

(XIII)

wherein A is hydroxyl, substituted hydroxyl, thiol, substituted thiol, amino, mono- or di-hydrocarbylsubstituted amino, or mono- or di-acylamino.

Preferably, A is hydroxyl, i.e. the compound of formula (X) is clavulanic acid or a pharmaceutically acceptable salt thereof, in particular an alkali metal salt.

The following Examples illustrate the preparation of some of the compounds of this invention. Temperatures are expressed in °C.

EXAMPLE 1

Sodium 6,α-methoxy-6,β-[2-(2-methylphenoxycarbonyl)-2(thien-3-yl)acetamido]penicillanate (i) Benzyl 6,α-methoxy-6,β-[2-(2-methylphenoxycarbonyl-2-(thien-3-yl)acetamido]penicillanate.

A solution of 2-methylphenyl hydrogen thien-3-ylmalonate (13.8 g) in diethylether (200 ml) was treated with DMF (6 drops) and oxalyl chloride (5 ml). After 1 hour at room temperature the reaction was evaporated to dryness in vacuo. The acid chloride was redissolved in dichloromethane (75 ml) and added dropwise to an ice-cold solution of benzyl 6,α-methoxy-6,β-aminopenicillanate (14.72 g) and pyridine (6.8 ml) in dichloromethane (150 ml). After 2 hours the solution was washed successively with 0.5 N hydrochloric acid (100 ml), water (100 ml), 1 N sodium bicarbonate solution (100 ml) and water (3×100 ml). After drying over magnesium sulphate and filtering the solution was evaporated to dryness in vacuo. The product was isolated by chromatography on silica eluting with ethyl acetate in light petroleum b.p. 60°–80°, 12.5% grading to 50%, yield 12.0 g, $\nu_{max}$ (CHCl$_3$) 1770, 1740, 1690 1485, 1315, 1170 and 1110 cm$^{-1}$, δ(CDCl$_3$) 1.32 (6H,s,2x2CH$_3$) 2.07 (3H,s,ArCH$_3$), 3.40, 3.42 (3H,2xs,OCH$_3$), 4.42 (1H,s,3H), 5.02(1H,s,CHCONH), 5.16(2H,s,OCH$_2$Ph), 5.58(1H,s,5H), 6.90–7.80 (13H,m,thien-3-yl,Ph,Ar,-CONH).

(ii) Sodium 6,α-methoxy-6,β-[2-(2-methylphenoxycarbonyl)-2-(thien-3-yl)acetamido]-penicillanate.

A solution of benzyl 6,α-methoxy-6,β-[2-(2-methylphenoxycarbonyl)-2-(thien-3-yl)acetamido]penicillanate (9 g) in ethanol (135 ml) and water (10 ml) was hydrogenated in the presence of 10% Pd/C (9 g). After 2 hours the catalyst was replaced and hydrogenation continued for 16 hours. The catalyst was filtered off and the solution was evaporated in vacuuo. The oil was dissolved in diethyl ether and treated with 2 N sodium 2-ethylhexanoate in 4-methylpentan-2-one (7.5 ml). The precipitated sodium salt was filtered off, washed thoroughly with ether and dried, yield 6.0 g, $\nu_{max}$ (KBr)3400(br), 1760, 1690, 1610, 1410 and 750 cm$^{-1}$; δ(D$_2$O) 1.43(6H,bs,2x2CH$_3$), 1.92 (3H,s,ArCH$_3$), 3.38, 3.50 (3H,2xs, OCH$_3$), 4.30(1H,s,3H), 5.63(1H,s,5H), 6.8–7.7 (7H,m,thien-3-yl,Ar). DMF=N,N-dimethylformamide

EXAMPLE 2

Sodium 6,α-methoxy-6,β-[2-(2-methylphenoxycarbonyl)-2-(thien-3-yl)acetamido]penicillanate 6,β-[2-Carboxy-2-(thien-3-yl)acetamido]-6,α-methoxypenicillanic acid (5.38 g, 13 mmole) in ethyl acetate (10 ml) was cooled in an ice bath and treated with o-cresol (1.54, 14.3 mmole) followed by N,N'-dicyclohexylcarbodiimide (3.24 g, 15.7 mmole). The mixture was stirred for 45 minutes then the precipitated dicyclohexylurea filtered off and washed with ethyl acetate (20 ml). The filtrate was extracted successively with 0.4 N sodium bicarbonate (25 ml), 0.2 N sodium bicarbonate (50 ml, 25 ml) then water (25 ml). The combined aqueous extracts were washed with ether then acidified to pH4.0 with 40% phosphoric acid and extracted with ether (3×50 ml). The ether solution was washed with water (2×50 ml) and saturated brine (25 ml) dried over magnesium sulphate and evaporated to a foam in vacuo, 3.81 g. This in ether (100 ml) was treated with 2 N sodium 2-ethylhexanoate in 4-methylpentan-2-one (3.78 ml) and the precipitated sodium salt collected, washed with ether and dried in vacuo, yield 3.45 g, identical with the material described in example 1ii).

EXAMPLE 3

Crystallisation of 6,α-methoxy-6,β-[R-2-(2-methylphenoxycarbonyl)-2-(thien-3-yl)acetamido]penicillanic acid 6,α-Methoxy-6,β-[2-(2-methylphenoxycarbonyl)-2-(thien-3-yl)acetamido]penicillanic acid (3.84 g, prepared as in example 2, 66% pure by h.p.l.c. assay) was dissolved in warm 4-methylpentan-2-one (8 ml) and set aside to crystallise overnight. The crystals were collected, washed with ether and dried in vacuo, yield 2.02 g, 96% pure by h.p.l.c. assay, $\nu_{max}$(KBr) 3340, 1755(b), 1697, 1492, 1333, 1155 and 1105 cm$^{-1}$, δ[(CD$_3$)$_2$CO] 1.32, 1.43(6H,2xs,2xCH$_3$), 2.19 (3H,s,ArCH$_3$), 3.58 (3H,s,OCH$_3$), 4.33(1H,s,3H), 5.51 (2H,s,5H,$\overline{CH}$CONH), 6.9–78(7H,m,thien-3-yl,Ar), 9.71(1H,s,$\overline{CONH}$), this nmr, run immediately after the solution was made up, showed the crystalline material to be a single diastereoisomer at the side chain methine. After 1 hour the spectrum had changed to show a mixture of R and S diastereoisomers, δ1.32, 1.43, 1.49, 1.52 (6H,4xs), 2.19, 2.21(3H,2xs), 3.32, 3.56(3H,2xs), 4.33, 4.38 (1H,2xs), 5.45 (1H,bs), 5.56, 5.58(1H,2xs), 6.9–7.8(7H,m), 9.24, 9.29(1H,2xs).

Diethyl ether and ethanol have been used as alternative crystallisation solvents.

A sample crystallised from diethyl ether had C,54.58,54.18; H, 4.76, 4.78; N, 5.40, 5.45; S, 12.36, 12.49%. C$_{23}$H$_{24}$N$_2$O$_7$S$_2$ requires C,54.75, H, 4.79; N, 5.55; S, 12.70%.

EXAMPLE 4

Acetoxymethyl 6,α-methoxy-6β-[2-(2-methylphenoxycarbonyl)-2-(thien-3-yl)-acetamido]penicillanate A solution of sodium 6,α-methoxy-6,β-[2-(2-methylphenoxycarbonyl)-2-(thien-3-yl)acetamido]penicillanate (1.03 g) and bromomethyl acetate (0.28 ml) in DMF (5 ml) was stirred at room temperature for 3 days, diluted with ethyl acetate (60 ml), washed with water (3×30 ml) and saturated brine (30 ml), dried over magnesium sulfate, filtered and evaporated to dryness in vacuuo. The product was isolated by chromatography on silica eluting with ethyl acetate in cyclohexane, 20% grading to 40%, yield 0.35 g, $\nu_{max}$ (CHCl$_3$) 1770, 1695, 1490, 1320 1165, and 980 cm$^{-1}$, δ(CDCl$_3$) 1.41(6H,s,2x2CH$_3$), 2.13, 2.17(3H,2xs,ArCH$_3$) 3.48, 3.53(3H,2xs,OCH$_3$),4.52(1H,s,3H), 5.24(1H,s,$\overline{CH}$CON), 5.72(1H,s,5H) 5.90

$$\overset{O}{\underset{\|}{\text{(2H, s, OCH}_2\text{OC)}},}$$

6.90–7.70 (7H,m,thien-3-yl,Ar), 8.10,8.20 (1H,2xs,CONH).

EXAMPLE 5

Pivaloyloxymethyl 6,α-methoxy-6,β-[2-(2-methylphenoxycarbonyl)-2-(thien-3-yl)-acetamido]penicillanate A solution of sodium 6,α-methoxy-6,β-[2-(2-methylphenoxycarbonyl)-2-(thien-3-yl)acetamido]penicillanate (1.03 g) and bromomethyl pivalate (0.58 g) in DMF (5 ml) was stirred at room temperature for 3 days, diluted with ethyl acetate (60 ml), washed with water (3×30 ml) and saturated brine (30 ml), dried over magnesium sulphate, filtered and evaporated to dryness in vacuuo. The product was isolated by chromatography on silica eluting with ethyl acetate in cyclohexane, 20% grading to 40%, yield 0.63 g, $\nu_{max}$ (CHCl$_3$) 1765(br, 1690, 1490, 1110 (br) and 980 cm$^{-1}$, δ(CDCl$_3$) 1.23[9H,s,C(CH$_3$)$_3$], 1.40, 1.43 (6H,2xs,2x2CH$_3$), 3.48, 3.52(3H,2xs,OCH$_3$), 4.51(1H,s,3H), 5.19 (1H,s,CHCON), 5.69 (1H,s,5H), 5.91

$$\overset{O}{\underset{\|}{\text{(2H, s, OCH}_2\text{OC)}},}$$

700–780(7H,m,thien-3-yl,Ar) 7.98, 8.10(1H,2xs,CONH).

EXAMPLE 6

Benzyl 6,α-methoxy-6,β-[2(2-methylphenoxycarbonyl)-2-(thien-3-yl)acetamido]penicillanate Benzyl 6,α-methoxy-6,β-[2-carboxy-2-(thien-3-yl)acetamido]penicillanate (5.04 g) in dichloromethane (20 ml) was cooled in an ice bath then treated with 2-methylphenol (1.08 g) followed by N,N'-dicyclohexylcarbodiimide (2.06 g). The mixture was stirred overnight, filtered and the filtrate evaporated to dryness. The residue was dissolved in ether (200 ml) then washed successively with water, N hydrochloric acid, water, 0.5 N sodium bicarbonate solution, water and brine, dried over anhydrous magnesium sulphate and evaporated to a foam (6.0 g), the spectral characteristics of which were identical to those of the material prepared in example 1(i).

EXAMPLE 7

Sodium 6,α-methoxy-6,β-[2-(2-methylphenoxycarbonyl)-2-(thien-3-yl)acetamido]penicillanate (i) 4-Nitrobenzyl 6,α-methoxy-6,β-[2-(2-methylphenoxycarbonyl)-2-thien-3-yl)acetamido]penicillanate 2-(2-Methylphenoxycarbonyl)-2-(thien-3-yl)acetyl chloride (prepared from 2-methylphenyl hydrogen thien-3-ylmalonate (11.86 g) as in example 1 (i)) in isopropyl acetate (15 ml) was added dropwise to 4-nitrobenzyl 6,β-amino-6,α-methoxypenicillanate (13.1 g) and pyridine (6.2 ml) in isopropyl acetate (85 ml) cooled to −12°. The mixture was diluted with dichloromethane (50 ml), stirred for 30 minutes then washed with water, N hydrochloric acid, water, saturated sodium bicarbonate solution, water and brine, then dried and evaporated to a yellow foam (20.9 g) δ(CDCl$_3$) 1.32 (6H, s, 2x2CH$_3$), 2.07 (3H, s, ArCH$_3$), 3.41 (3H, s, OCH$_3$), 4.44, 4.45 (1H, 2xs, 3H), 5.02 (1H, s, $\overline{CH}$CONH), 5.19 and 5.28 (2H, ABq, J 13 Hz, OCH$_2$Ph($\overline{p}$NO$_2$)), 5.55 (1H, s, 5H), 6.8–7.5 (7H, m, thienyl and —C$_6$H$_4$CH$_3$), 7.50 and 8.18 (4H, ABq, J 8 Hz, OCH$_2$$\underline{Ph}$(pNO$_2$)), 7.60, 7.72 (1H, 2xs, CONH).

(ii) Sodium 6,α-methoxy-6,β-[2-(2-methylphenoxycarbonyl)-2-(thien-3-yl)acetamido]penicillanate Hydrogenation of 4-nitrobenzyl 6, -methoxy-6,β[2-(2-methylphenoxycarbonyl)-2-(thien-3-yl)acetamido]- penicillanate in ethyl acetate as described in example 1 (ii) gave material identical with that in example 1 (ii).

Biological Data

Comparison with 6β-[2-(phenoxycarbonyl)-2-thien-3'-ylacetamido]-6α-methoxy penicillanic acid in human bioavailability studies.

At a dose equivalent to 100 mg of 6β-[2-(carboxy)-2-thien-3'-ylacetamido]-6α-methoxy penicillanic acid the urine recoveries of 6β-[2-(carboxy)-2-thien-3'-ylacetamido]-6α-methoxy penicillanic acid were:

6β-[2-(phenoxycarbonyl)-2-thien-3'-ylacetamido]-6α-methoxy penicillanic acid gave 11% urine recovery.

6α-[2-(2'-methylphenoxycarbonyl)-2-thien-3'-ylacetamido]-6α-methoxy penicillanic acid gave 33% urine recovery.

What we claim is:

1. 6,α-Methoxy-6,β-[2-(2'-methylphenoxycarbonyl)-2-(thien-3'-yl)acetamido]penicillanic acid of formula (II):

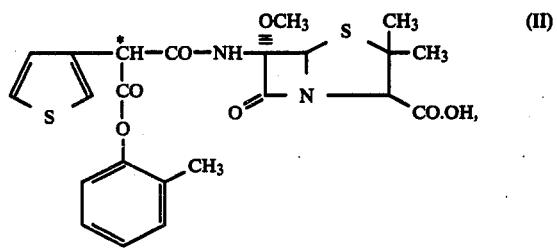

a pharmaceutically acceptable salt thereof or an in vivo hydrolysable ester thereof.

2. The compound according to claim 1 which is 6,α-methoxy-6,β-[2-(2'-methylphenoxycarbonyl)-2-(thien-3'-yl)acetamido]penicillanate.

3. The compound according to claim 1 which is 6,α-Methoxy-6,β-[R-2-(2'-methylphenoxycarbonyl)-2-(thien-3'-yl)acetamido]penicillanic acid.

4. The compound according to claim 1 which is crystalline 6,α-methoxy-6,β-[R-2-(2'-methylphenoxycarbonyl)-2-(thien-3'-yl)acetamido]penicillanic acid.

5. An intermediate of the formula (X):

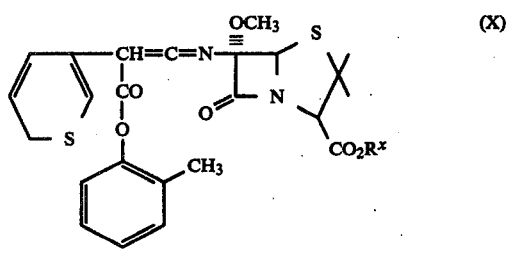

wherein $R^x$ is a carboxyl blocking group.

6. A pharmaceutical composition useful for treating bacterial infections in humans and animals which comprises an antibacterially effective amount of 6,α-methoxy-6,β-[2-(2'-methylphenoxycarbonyl)-2-(thien-3'-yl)acetamido]penicillanic acid of formula (II):

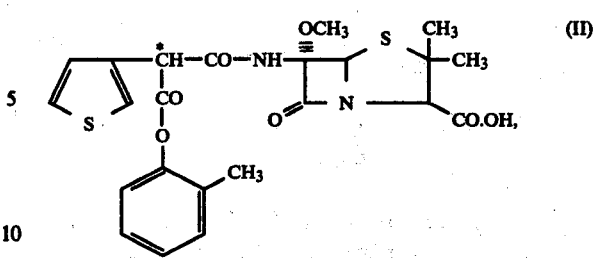

a pharmaceutically acceptable salt thereof or an in-vivo hydrolysable ester thereof, in combination with a pharmaceutically acceptable carrier.

7. A composition according to claim 6 in oral administration form.

8. A composition according to claim 6 wherein the compound is sodium 6,α-methoxy-6,β-[2-(2'-methylphenoxycarbonyl)-2-(thien-3'-yl)acetamido]penicillanate.

9. A composition according to claim 6 wherein the compound is 6,α-methoxy-6,β-[R-2-(2'-methylphenoxycarbonyl)-2-(thien-3'-yl)acetamido]penicillanic acid.

10. A composition according to claim 6 wherein the compound is crystalline 6,α-methoxy-6,β-[R-2-(2'-methylphenoxycarbonyl)-2-(thien-3'-yl)acetamido]penicillanic acid.

11. A method of treating bacterial infections in humans and animals which comprises administering to a human or animal in need thereof an antibacterially effective amount of 6,α-methoxy-6,β-[2-(2'-methylphenoxycarbonyl)-2-(thieny-3'-yl)acetamido]penicillanic acid of the formula (II):

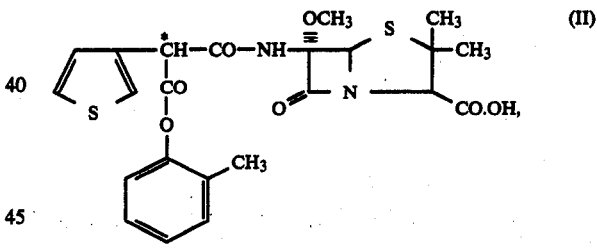

a pharmaceutically acceptable salt thereof or an in-vivo hydrolysable ester thereof, in combination with a pharmaceutically acceptable carrier.

12. A method according to claim 11 wherein the administration is oral.

13. A method according to claim 11 wherein the compound is sodium 6,α-methoxy-6,β-[2-(2'-methylphenoxycarbonyl)-2-(thien-3'-yl)acetamido]penicillanate.

14. A method according to claim 11 wherein the compound is 6,α-methoxy-6,β-[R-2-(2'-methylphenoxycarbonyl)-2-(thien-3'-yl)acetamido]penicillanic acid.

15. A method according to claim 11 wherein the compound is crystalline 6,α-methoxy-6,β-[R-2-(2'-methyl-phenoxycarbonyl)-2-(thien-3'-yl)acetamido]penicillanic acid.

16. A pharmaceutical composition useful for treating bacterial infections in humans and animals which comprises a synergistically effective amount of a compound of the formula (XIII):

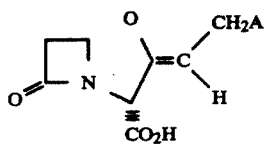

or a pharmaceutically acceptable salt thereof or a pharmaceutically acceptable ester thereof, wherein A is hydroxyl, substituted hydroxyl, thio, substituted thio, amino, mono- or di-hydrocarbyl-substituted amino, or mono- or di-acylamino, and an antibacterially effective amount of a penicillin according to claim 1, in combination with a pharmaceutically acceptable carrier.

17. A composition according to claim 16 wherein the compound of the formula (XIII) is clavulanic acid or an alkali metal salt thereof.

18. A composition according to claim 17 which contains potassium clavulanate and sodium 6,α-methoxy-6β-[2-(2'-methylphenoxycarbonyl)-2-(thien-3'-yl)acetamido]penicillanate.

19. A method of treating bacterial infections in humans and animals which comprises administering to a human or animal in need thereof a synergistically effective amount of a compound of the formula (XIII):

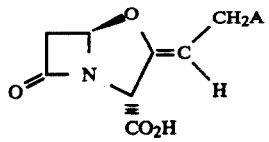

or a pharmaceutically acceptable salt thereof or a pharmaceutically acceptable ester thereof, wherein A is hydroxyl, substituted hydroxyl, thio, substituted thio, amino, mono- or di-hydrocarbyl-substituted amino, or mono- or di-acylamino, and an antibacterially effective amount of a penicillin according to claim 1, in combination with a pharmaceutically acceptable carrier.

* * * * *